United States Patent
Mathonnet et al.

(10) Patent No.: US 8,859,487 B2
(45) Date of Patent: Oct. 14, 2014

(54) PERFUME TESTERS OR PERFUMES

(75) Inventors: Jean-Pierre Mathonnet, Frejus (FR); Gaetano Zannini, Biot (FR)

(73) Assignee: Laboratoires Docteur Gaetano Zannini, Saint Raphael (FR)

( * ) Notice: Subject to any disclaimer, the term of this patent is extended or adjusted under 35 U.S.C. 154(b) by 605 days.

(21) Appl. No.: 12/375,495

(22) PCT Filed: Jul. 30, 2007

(86) PCT No.: PCT/FR2007/001311
§ 371 (c)(1),
(2), (4) Date: Apr. 20, 2009

(87) PCT Pub. No.: WO2008/012450
PCT Pub. Date: Jan. 31, 2008

(65) Prior Publication Data
US 2009/0312230 A1    Dec. 17, 2009

(30) Foreign Application Priority Data
Jul. 28, 2006    (FR) .................... 06 06921

(51) Int. Cl.
| | | |
|---|---|---|
| *A61K 8/00* | (2006.01) | |
| *A61K 8/18* | (2006.01) | |
| *A61Q 13/00* | (2006.01) | |
| *A61L 9/04* | (2006.01) | |
| *C11D 3/50* | (2006.01) | |
| *A61Q 1/14* | (2006.01) | |
| *A61Q 19/10* | (2006.01) | |
| *A61Q 19/00* | (2006.01) | |
| *C11D 9/20* | (2006.01) | |
| *C11D 17/00* | (2006.01) | |
| *A01N 25/34* | (2006.01) | |
| *A61K 9/48* | (2006.01) | |
| *A61K 9/14* | (2006.01) | |
| *A61K 9/50* | (2006.01) | |
| *A61K 8/02* | (2006.01) | |
| *A61K 8/92* | (2006.01) | |
| *A61K 8/97* | (2006.01) | |

(52) U.S. Cl.
CPC ................ *A61K 8/92* (2013.01); *A61K 8/0204* (2013.01); *A61K 2800/56* (2013.01); *A61Q 13/00* (2013.01); *A61K 8/97* (2013.01)
USPC ................... 512/4; 512/1; 510/130; 510/396; 510/403; 510/532; 424/408; 424/451; 424/485; 424/502

(58) Field of Classification Search
CPC ........... A61Q 13/00; A61K 8/92; A61K 8/97; A61K 8/0204; A61K 2800/56
USPC ................. 512/1, 4; 424/408, 451, 485, 502; 510/130, 396, 403, 532
See application file for complete search history.

(56) References Cited

U.S. PATENT DOCUMENTS 2,300,769 A * 11/1942 Berry .............................. 239/54
3,539,465 A * 11/1970 Heistand et al. ........... 428/402.2
(Continued)

FOREIGN PATENT DOCUMENTS

| DE | 2731318 A1 | 2/1979 |
|---|---|---|
| DE | 199 41 263 A1 | 3/2001 |

(Continued)

OTHER PUBLICATIONS

Barbosa-Canovas ed. Food Powders, Chapter 8 pp. 199-219; Springer Apr. 2005.*

(Continued)

*Primary Examiner* — Patrick Ryan
*Assistant Examiner* — Aaron Greso
(74) *Attorney, Agent, or Firm* — Westerman, Hattori, Daniels & Adrian, LLP

(57) ABSTRACT

A perfume tester or perfume includes a granule containing a friable peripheral portion incorporating fragrant compounds, which disintegrates as a perfumed powder when the granule is applied onto the skin. A method for making the perfume tester or perfume is by granulation, and the granule can be used in particular for perfume testing.

23 Claims, 2 Drawing Sheets

(56) References Cited

U.S. PATENT DOCUMENTS

| | | | |
|---|---|---|---|
| 5,004,595 A * | 4/1991 | Cherukuri et al. | 424/48 |
| 5,271,881 A * | 12/1993 | Redding, Jr. | 264/4.32 |
| 6,013,610 A | 1/2000 | Leu | |
| 6,235,274 B1 * | 5/2001 | Lou et al. | 424/65 |
| 6,550,474 B1 * | 4/2003 | Anderson et al. | 128/200.24 |
| 7,052,856 B2 * | 5/2006 | Ting | 435/7.21 |
| 2002/0086042 A1 * | 7/2002 | Delrieu et al. | 424/401 |
| 2002/0187223 A1 * | 12/2002 | McIver et al. | 426/96 |
| 2003/0194416 A1 | 10/2003 | Shefer et al. | |
| 2003/0195133 A1 | 10/2003 | Shefer et al. | |
| 2005/0020634 A1 * | 1/2005 | Terashita et al. | 514/337 |
| 2005/0176598 A1 | 8/2005 | Bergquist et al. | |

FOREIGN PATENT DOCUMENTS

| | | | | |
|---|---|---|---|---|
| JP | 61-37721 A | 2/1986 | | |
| JP | 61-87618 A | 5/1986 | | |
| JP | 3-82471 A | 4/1991 | | |
| WO | WO2005079598 | * | 9/2005 | A23L 1/22 |

OTHER PUBLICATIONS

Defined Media for Aspen Tissue Culture 1966, p. 1, last paragraph Institute of Paper Chemistry Appleton WI Project 2351.*
Rebeyrolle et al. Journal of Applied Polymer Science vol. 44 No. 10 pp. 1787-1793 1992.*
Novotna et al Restaurator vol. 23 No. 4 pp. 256-269 2002.*
Al Root Company, C.C. Miller, Gleanings in Bee Culture 1897 vol. XXV No. 1 pp. 283-284.*
Ecroyd Beekeeping Supplies LTD (p. 1 2004).*
Hassler Virchows Arch. Abt. A. Path. Anat. vol. 352 pp. 26-33 1971.*
Magoori et al Journal of Biological Chemistry Mar. 28, 2003 vol. 278 No. 13 pp. 11331-11336.*
International Search Report of PCT/FR2007/001311, mailing date of Jan. 18, 2008.

* cited by examiner

US 8,859,487 B2

PERFUME TESTERS OR PERFUMES

This application is a U.S. national stage of PCT Application No. PCT/FR2007/001311, field Jul. 30, 2007, and claims priority of French application No. 0606921 filed Jul. 28, 2006.

The invention relates to granules, perfume testers or perfumes, methods for making them and uses thereof.

Testers are used in order to assess perfumes in terms of olfaction. The testers known from the prior art are small vials generally made of glass that contain a few milliliters of perfume as a liquid mainly including an alcoholic carrier and fragrant compounds. Actually, these are very often scaled models of vials intended to be sold with cap, dropper or spraying device.

These known testers have many drawbacks. First, they are fragile and not always entirely watertight. Moreover, they are not wholly suitable for the use they are made for. Indeed, when a user chooses to test a perfume onto the skin, he/she spreads this liquid perfume onto a skin area generally located at the back of his/her hand or on the forehand. However, the amount of perfume laid down on the skin area is not easily controlled by the user, even when the latter uses, combined with the testing vial, a dropper or spraying device. Moreover, the user generally spreads, onto the skin area chosen, too much perfume to allow a good quality test. Of course, it is possible to spread the perfume, not onto the skin, but onto a blotting paper strip. However, the perfume is then assessed in the atmosphere, under conditions very different from the actual conditions, which modifies the assessment of the mixture making up the fragrant compounds of the perfume in terms of olfaction.

In view of the foregoing, a problem that the invention proposes to solve is to provide a granule, perfume tester or perfume that has not the aforementioned drawbacks of the tester of the prior art, and that enables in particular to carry out tests on precise skin areas.

The first aim of the solution to this stated problem as proposed in the invention is a granule, characterised in that it contains a friable peripheral portion incorporating fragrant compounds, said friable peripheral portion being able to be disintegrating as a perfumed powder when said granule is applied onto the skin, and in that it has an average diameter greater than about 4 mm.

Moreover, the second aim is a method for making a granule such as defined above, characterised in that it implements a granulation.

The third aim is the use of a granule as defined above, characterised in that said granule is applied onto the skin such that its friable peripheral portion is disintegrated.

The fourth aim is the use of a granule such as defined above, as a perfume tester.

Finally, the fifth and last aim is the use of a granule such as defined above, as a perfume.

Advantageously, —the granule according to the invention further contains an inner portion forming a hard core, this inner portion being made up differently from the peripheral portion; —the granule is substantially spherical with an average diameter between about 4 mm and about 30 mm; and preferably, between about 8 mm and about 15 mm; —the average diameter of the inner portion of the core-forming granule is greater than about 2 mm and the thickness of the peripheral portion of said granule is greater than about 1 mm; —the friable peripheral portion comprises fragrant compounds, a binder and an inert carrier made of a powder; —the binder contains a wax; —the core-forming inner portion comprises between 2 and 50% in weight of the total weight of said gum portion; —the granule does not contain a hard core and is formed of a mass of controlled friability to release a perfumed powder by being disintegrated under the effect of frictions with the skin or of a sufficient pressure being applied; —the method for making a granule includes the following steps of: carrying out a granulation in the presence of a crystallised powdery solid phase and a liquid or pasty phase comprising a gum and a perfume; producing one or more consecutive coatings by spraying the liquid or pasty phase and dusting the crystallised solid phase; carrying out a drying of the cores thus obtained; producing a peripheral portion by spraying a liquid or pasty phase comprising in particular a wax and dusting the crystallised solid phase; and carrying out a drying of the coated granules obtained comprising a core and a peripheral portion; and—the perfume is delivered as a dry form of the perfumed powder, after said granule or its peripheral portion is disintegrated, under the effect of frictions of the granule onto the skin or of a sufficient pressure being applied.

The granule, tester or perfume according to the invention is thereby as a solid form. Applying a tester is carried out on a precise skin area defined by its movement directly on the skin. It is possible to thereby test a plurality of perfumes or even to contemplate, with testers comprising different perfumes, perfume superposition testing.

The invention will be better understood upon reading the following non-limiting description and the appended drawings, wherein.

Figure 1:
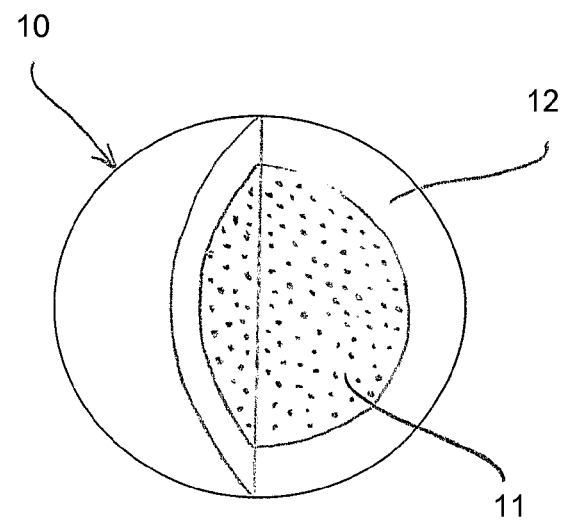
FIG. 1 shows, in perspective, a granule, perfume tester or perfume according to the invention, made up of a core containing a peripheral portion and a core-forming inner portion.

In FIG. 1, there is shown a granule, perfume tester or perfume according to the invention. This perfume tester or perfume comprises a substantially spherical granule 10 with an average diameter greater than about 4 mm, and preferably between about 4 mm and about 30 mm and, even more preferably, between about 8 mm and about 15 mm.

In a preferred embodiment according to the invention, the granule contains, on the one hand, a core-forming interior or inner portion 11 and, on the other hand, a peripheral portion 12 making up a shell.

The core 11 is substantially spherical with an average diameter greater than about 2 mm, preferably between about 5 mm and about 10 mm. The core 11 contains possible several sublayers made by consecutively coating a central part. However, its composition is homogeneous from its central part to its periphery. Moreover, the core 11 is stable, compact and has some hardness. This hardness is such that a user of the tester according to the invention, that would apply a moderate pressure onto the surface of the core 11 by holding it between his/her thumb or his/her forefinger, could not disintegrate it.

The core 11 comprises between 2% and 50% and, preferably between 5 and 20% in weight of gums, in particular vegetable and/or synthetic ones. By way of non-limiting examples of gums likely to be used for making the core 11, it will be set out water-soluble gums such as gum arabic, carrageenans, alginates, pectins, karaya gum, xanthan gum, chitosan or derivatives thereof, hyaluronic acid, pullulan polymers or agar, dextran, celluloses and derivatives thereof such as methylcellulose or hydroxypropylcellulose, acrylic acid polymers cross-linked with an allyl ether, such as those known as carbomers, substantially made of a carbomer or a carbomer mixture such as the acrylic acid polymers cross-linked with polyalkenyl ethers under the trade name Carbopol™. The core further comprises 20% to 80% in weight of an inert crystallised substance such as talc or any other inert crystallised substances for cosmetic purposes. Finally, it comprises a residual amount of water, for example between about 1% and about 6% in weight of the total weight of the core, a residual amount of alcohol and fragrant compounds.

The shell 12 is as a layer covering the entire core 11. Even though this is not generally the case, it is likely to be composed of a plurality of sublayers. The thickness of the shell 12 is substantially constant along the surface of the core 11. In practice, it is greater than about 1 mm and, preferably, in the order of 2 mm. The hardness of the shell 12 is much smaller than that of the core 11 such that, unlike the core 11, the shell 12 is friable. This friability is such that, under the effect of a moderate pressure that would be applied by a user holding a tester according to the invention between his/her thumb and his/her forefinger, the shell 12 would be disintegrated as the fragrant powder of fine fragrant particles with an average diameter of a few microns.

The fragrant powder, perfuming or perfumed, can also have the form of a fine layer, more or less homogeneous depending on the amount of binder contained in the peripheral layer 12 of the granule 10, left onto the skin after being applied and/or rubbed by a user and after the shell 12 is disintegrated.

The shell 12 is chemically different from the core 11. Indeed, the shell 12 comprises a substantial amount of an insulating, substantially impervious and film-forming binder. Thanks to this binder, the evaporation of the fragrant compounds is limited. The binder, present in an amount of more than 1% in weight of the total weight of the shell 12, consists in particular of natural waxes, of animal or plant origin, or artificial waxes. By way of non-limiting examples of waxes for composing the binder of the shell 12, it will be set out bee or carnauba wax, paraffin, vegetable oils, microcrystalline wax or silicone waxes. It can further be set out wax mixtures such as mixtures including bee and carnauba waxes. Moreover, the shell 12 comprises a substantial amount of perfume compounds. Indeed, and as will be detailed in the continuation of the present description, for making the shell 12, a mixture is used comprising more than 40% and up to 70% in weight of a liquid perfume whose alcoholic carrier is thereafter largely evaporated. Furthermore, the shell 12 comprises an inert solid carrier consisting of a substance crystallised into fine particles. It is for example talc or any other inert crystallised substances for cosmetic purposes. In practice, the crystallised substance chosen will be identical to the one used for making up the core 11. Finally, the shell 12 comprises a residual amount of alcohol.

In another embodiment of the perfume tester or perfume according to the invention, the granule does not contain a hard core. It is then formed of a relatively homogeneous mass whose friability is controlled for releasing powder by disintegrating in particular its periphery under the effect of frictions with the skin or of a sufficient pressure being directly applied onto the skin. However, it will be noted that the entire granule is likely to be friable such that a person for example wishing to put on perfume or to perfume an object or solution, breaks up the granule as a perfuming powder.

For making a perfume tester or perfume according to the invention, the so-called Technabio™ granulation method disclosed in the patent document published as WO97/04861 is advantageously used, which implements a granulator provided with a rotary turbine such as a sugar-coating turbine.

For making a perfume tester or perfume according to the invention, the so-called Technabio™ II granulation method is even more advantageously used which includes a dynamic drying step, for example in the order of 15 minutes.

Figure 2:
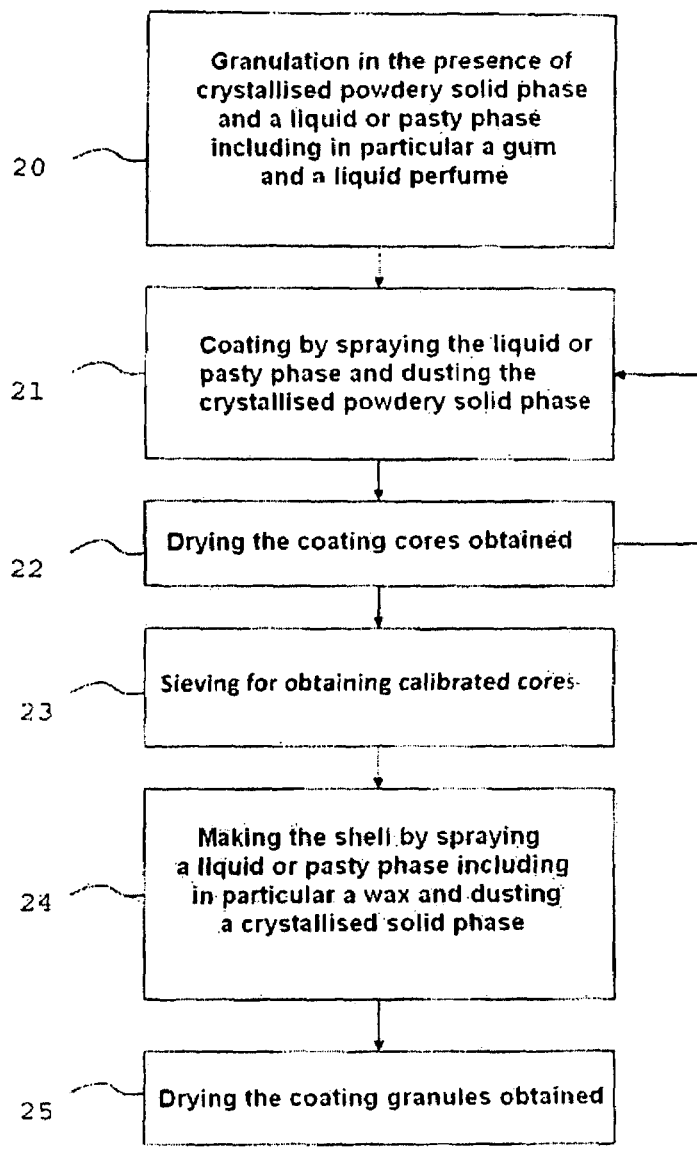
FIG. 2 illustrates the different steps of a method for making a granule, perfume tester or perfume according to the invention.

In a first step 20 of the method according to the invention mentioned in FIG. 2, a granulation is carried out in the presence of a powdery solid phase formed of the inert crystallised substance and a liquid or pasty phase comprising the gum, a perfume comprising an alcoholic carrier and fragrant compounds, water and alcohol. The liquid or pasty phase components can be sequentially added. From the quantitative point of view, if, for example, 100 g of powdery solid phase are used for the granulation, between 5 to 15 g of gum, 25 to 45 g of water, 25 to 45 g of alcohol and 10 to 30 g of perfume will then be used. The granulation is substantially carried out at room temperature and in the presence of a hygrometry less than 70%.

The desired final dimensions of the core 11 are achieved by consecutive coatings. These coatings are produced by spraying the aforementioned liquid or pasty phase and then dusting the crystallised powdery solid phase (step 21, FIG. 2). A drying 22 is carried out after each coating step 21. The drying temperature is between about 40° C. and about 55° C. and, preferably, between about 45° C. and about 50° C. The drying time is greater than 30 min, for example in the order of 1h30.

For obtaining calibrated cores, a sieving 23 is carried out. The sieve meshes are designed for obtaining cores 11 with a desired gauge.

The subsequent steps relate to the manufacturing of the outer shell 12.

For making such shell 12, a liquid or pasty phase is first prepared comprising the wax, a perfume in a conventional form comprising an alcoholic carrier and fragrant compounds, and alcohol. From the quantitative point of view, this liquid or aqueous phase contains between 30 and 50% in weight of wax, between 40 and 70% in weight of perfume and between 5 and 10% in weight of alcohol, the percentages being given by weight of the total weight of the considered phase.

Then, this liquid or pasty phase is sprayed onto the cores 11 (step 24, FIG. 2). This phase in particular provides adhesion of the shell 12 to the core 11. Then, all this is dusted with the inert crystallised powdery phase. Then, a last drying 25 is carried out at temperatures between about 40° C. and about 55° C. and, preferably, between about 45° C. and about 50° C., for example in the order of 45° C. in order to obtain tester- or perfume-forming perfumed granules according to the invention.

These testers or perfumes are likely to be stored and kept for a relatively long time, for example for about several months, without altering their fragrant qualities.

Figure 3:
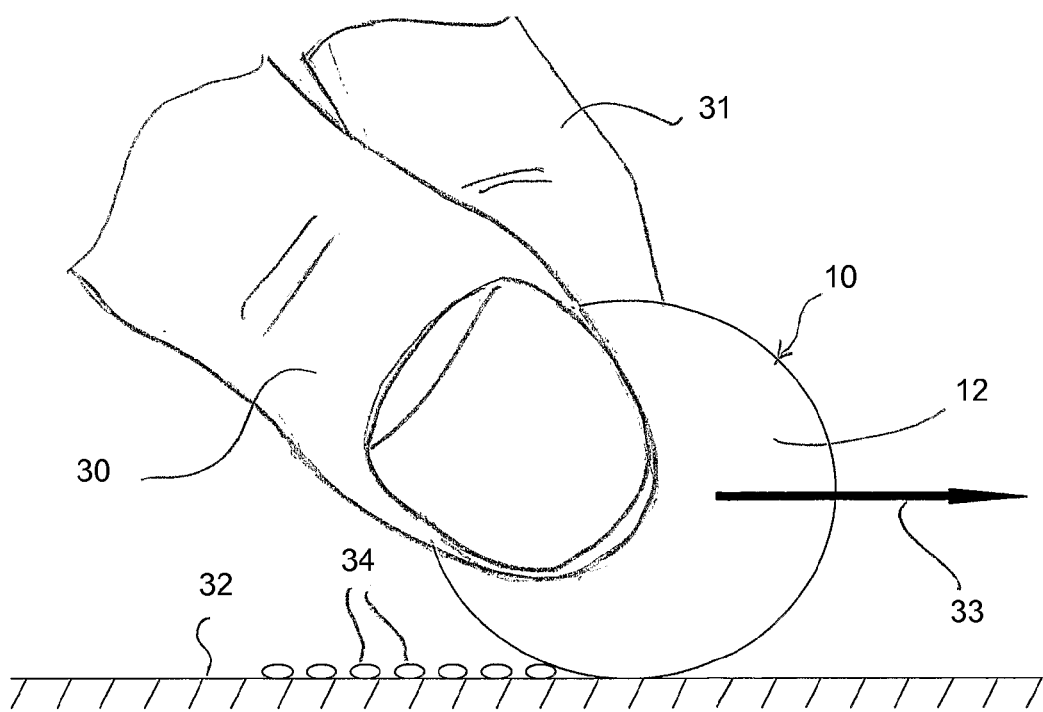
FIG. 3 shows, in perspective, a mode for using a granule, perfume tester or perfume according to the invention, when applied onto the skin.

As it is shown in FIG. 3, to carry out a test, a user takes a granule 10 according to the invention between his/her thumb 30 and his/her forefinger 31. Then, he/she applies this tester forming granule 10 to the surface of a skin area 32 he chooses, for example on the back of his/her hand. He/she applies a slight pressure onto the tester and moves it along the skin area chosen, for example in the direction of the arrow 33. The pressure and the frictions generated by the tester moved in contact with the skin causes the friable shell 12 to be degraded, which can leave a fragrant powdery streak 34. Only the shell 12 is degraded. Being harder, the core 11 preserves its integrity. The area of the powdery streak, which exactly corresponds to the fragrant area, is accurately bounded by the movements of the tester at the skin surface. The user has then just to smell this area to fully assess the perfume and check the compatibility thereof with his/her skin. The powdery streak can thereafter be easily removed. However, if the user wishes to test another perfume, he/she then just has to choose another tester prepared with this other perfume and apply this tester to another skin area. It will be easy for him/her to differentiate the areas, considering the powdery streaks left by the tests. The user can even, if he/she wishes, carry out perfume or smell association tests. For this, indeed, he/she just has to carry out a first test with a first perfume or smell and then to carry out a second test with a second perfume or smell in his/her skin area surrounding the area of the first test or on the same area, and to smell the perfume or smell superposition.

The smell substantially comes from the fragrant compounds associated to the inert carrier of the shell degraded under the effect of frictions between the tester and the skin. Therefore, this is a solid tester delivering a perfume as a dry and not liquid form, as in the prior art. Furthermore, this dry perfume source does not substantially include alcohol. Thus, people who do not wish or cannot be in contact with alcohol for medical, ethnic or religious reasons, will then be able to test perfumes with a tester according to the invention, or even put on perfume with a perfume according to the invention.

After the test, the user can keep the perfume tester. Once perfumed in its mass, the compact core will release a pleasant perfumed feeling for many weeks.

The examples below relate to the manufacturing of perfume testers according to the invention.

Example 1

So-Called Serena™ Perfume Testers

A granulation is carried out according to the Technabio™ method from equal amounts of a powdery solid phase of talc and of the following liquid phase, the percentages being given by weight of the total weight of the liquid phase:

| | |
|---|---|
| Water | 35.00% |
| Gum arabic | 10.00% |
| 50° Alcohol | 35.00% |
| Liquid Serena ™ Perfume | 20.00% |

The components of the liquid phase are added in the following order: water, gum arabic, alcohol and then Serena™ perfume.

8 consecutive coatings are produced for making the core. The weights of the liquid and powdery phases are measured before and after coating and the material incorporation percentages are calculated. The results contained in the following table 1 are obtained:

TABLE 1

| | Weight before (g) | Weight after (g) | Consumption in g | Incorporation percentage |
|---|---|---|---|---|
| N° 1 | | | | |
| Liquid phase | 352.05 | 342.19 | 9.86 | 17.33% |
| Powdery phase | 937.5 | 880.6 | 56.9 | |
| N° 2 | | | | |
| Liquid phase | 342.19 | 329.96 | 12.23 | 23.66% |
| Powdery phase | 880.6 | 828.9 | 51.7 | |
| N° 3 | | | | |
| Liquid phase | 329.96 | 307.54 | 22.42 | 19.96% |
| Powdery phase | 828.9 | 716.6 | 112.3 | |
| N° 4 | | | | |
| Liquid phase | 307.54 | 282.29 | 25.25 | 19.73% |
| Powdery phase | 716.6 | 588.6 | 128 | |
| N° 5 | | | | |
| Liquid phase | 282.29 | 261.34 | 20.95 | 23.27% |
| Powdery phase | 1085.3 | 995.28 | 90.02 | |
| N° 6 | | | | |
| Liquid phase | 261.34 | 208.5 | 52.84 | 22.93% |
| Powdery phase | 1000 | 769.6 | 230.4 | |
| N° 7 | | | | |
| Liquid phase | 204.5 | 189.36 | 15.14 | 23.77% |
| Powdery phase | 769.6 | 705.9 | 63.7 | |
| N° 8 | | | | |
| Liquid phase | 189.96 | 168.56 | 21.4 | 22.06% |
| Powdery phase | 705.9 | 608.9 | 97 | |
| Average Incorporation | | | | 18.62% |

The drying of the granules thus obtained is carried out in an oven for 1 hour, at temperatures between 45 and 50° C. Then, a sieving is carried out with 5, 6 and 6.5 mm diameter meshes. Calibrated granules with 460 g average weight are then obtained. These granules make up the cores of the testers according to the invention.

To produce friable shells, a second solution of the following composition is prepared:

| | |
|---|---|
| 50° Alcohol | 10 g |
| Wax mixture | 40 g |
| Perfume | 50 g |
| 90° Alcohol | 10 g |

A coating of the calibrated cores after sieving is produced in the aforementioned granulator for three ranks. The total weight of the cores before coating is 460 g and the total weight of the tester-forming granules, after coating and drying for 30 min, is 548.6 g.

Example 2

So-Called Prunelle™ Perfume Testers

A granulation according to the Technabio™ method is carried out from equal amounts of a powdery solid phase of talc and of the following liquid phase, the percentages being given by weight of the total weight of the liquid phase:

| | |
|---|---|
| Water | 35.00% |
| Gum arabic | 10.00% |
| 50° Alcohol | 35.00% |
| Liquid Prunelle ™ Perfume | 20.00% |

The components of the liquid phase are added in the following order: water, gum arabic, alcohol and then Prunelle™ perfume.

8 consecutive coatings are produced for making the core. The weights of the liquid and powdery phases are measured before and after coating and the material incorporation percentages are calculated. The results contained in the following table 2 are obtained:

TABLE 2

|  | Weight before (g) | Weight after (g) | Consumption in g | Incorporation percentage |
|---|---|---|---|---|
| N° 1 | | | | |
| Liquid phase | 270.9 | 261.52 | 9.38 | 12.96% |
| Powdery phase | 1055.6 | 983.2 | 72.4 | |
| N° 2 | | | | |
| Liquid phase | 261.52 | 248.8 | 12.72 | 15.77% |
| Powdery phase | 983.2 | 902.54 | 80.66 | |
| N° 3 | | | | |
| Liquid phase | 248.8 | 230.18 | 18.62 | 19.12% |
| Powdery phase | 902.54 | 805.18 | 97.36 | |
| N° 4 | | | | |
| Liquid phase | 230.18 | 218.26 | 11.92 | 20.07% |
| Powdery phase | 805.18 | 745.8 | 59.38 | |
| N° 5 | | | | |
| Liquid phase | 218.26 | 194.47 | 23.79 | 14.55% |
| Powdery phase | 745.8 | 582.24 | 163.56 | |
| N° 6 | | | | |
| Liquid phase | 197.47 | 167.11 | 30.36 | 22.60% |
| Powdery phase | 776.6 | 642.28 | 134.32 | |
| N° 7 | | | | |
| Liquid phase | 220.2 | 173.67 | 46.53 | 21.62% |
| Powdery phase | 940.1 | 724.9 | 215.2 | |
| N° 8 | | | Shell | |
| Liquid phase | 207.33 | 171.5 | 35.83 | 23.03% |
| Powdery phase | 1066.68 | 911.1 | 155.58 | |
| Average Incorporation | | | | 16.01% |

The drying of the granules thus obtained is carried out in an oven for 1 hour, at temperatures between 45 and 50° C. Then, a sieving is carried out with 5, 6 and 6.5 mm diameter meshes. Calibrated granules with 210 mg average weight are then obtained. These granules make up the cores of the testers according to the invention.

To produce the shell, a second solution of the following composition is prepared:

| | |
|---|---|
| Wax mixtures | 40 g |
| Prunelle ™ Perfume | 50 g |
| 50° Alcohol | 10 g |

A coating of the calibrated cores after sieving is produced in the aforementioned granulator for three ranks. The total weight of the tester-forming granules, after coating and drying for 30 min, is 548.6 g, when 400 g of granule cores are used.

Of course, the invention should be understood in a broad sense as encompassing embodiments of perfume testers or perfume or variants thereof that are not specifically described in the present description but that would be similar to the embodiments described or that could be inferred from the features of the invention by common operations implemented by those skilled in the art.

In particular, making the testers or perfumes according to the invention can be carried out with a fluidised bed or by means of any other devices or apparatuses able to make granules.

The invention claimed is:

1. A granule containing (i) an inner portion forming a core, and (ii) a friable peripheral portion forming a shell, wherein the granule has an average diameter greater than about 4 mm, wherein the core is harder than the shell and comprises:
   a gum in an amount of from 5 to 50% by weight of the core, and
   an inert crystallized substance being talc in an amount from 20 to 80% by weight of the core, and wherein the friable shell has a composition different from the core and comprises:
   a binder containing a wax, wherein the wax is present in an amount of more than 1% by weight of the shell,
   fragrant compounds which are residues in dry form of a liquid perfume that has been dried, wherein the fragrant compounds are present in the shell in an amount resulting from having dried a mixture comprising the wax and liquid perfume, wherein the wax is present in an amount of from 30 to 50% by weight of the mixture before drying and liquid perfume is present in an amount of 40 to 70% by weight of the mixture before drying, and
   an inert carrier made of a powder, wherein said powder contains particles of a crystallised substance, wherein the powder is present in the shell in an amount such that the shell is less hard than the core, so that said friable peripheral portion disintegrates as a perfumed powder under a moderate friction or pressure that does not disintegrate the core.

2. The granule according to claim 1, which is substantially spherical with an average diameter between about 4 mm and about 30 mm.

3. The granule according to claim 1, wherein an average diameter of the core-forming inner portion of the granule is greater than about 2 mm and a thickness of the peripheral portion of said granule is greater than about 1 mm.

4. A method for making a granule comprising implementing a granulation so as to obtain a granule according to claim 1.

5. The method according to claim 4, comprising the following steps:
   carrying out a granulation in the presence of a crystallised powdery solid phase and a liquid or pasty phase comprising a gum and a perfume;
   producing one or more consecutive coatings by spraying the liquid or pasty phase and dusting the crystallised solid phase;
   carrying out a drying of the cores thus obtained;
   producing a peripheral portion by spraying a liquid or pasty phase comprising fragrant compounds and a wax and dusting a powder containing particles of a crystallised substance; and
   carrying out a drying of the coated granules obtained comprising a core and a peripheral portion.

6. A method of using a granule according to claim 1, comprising applying said granule onto the skin such that its friable peripheral portion is disintegrated.

7. The method according to claim 6, wherein the granule is used as a perfume tester.

8. The method according to claim 6, wherein the granule is used as a perfume.

9. The method according to claim 8, wherein the perfume is delivered as a dry form of a perfumed powder, after said granule or its peripheral portion has been disintegrated, under the effect of frictions of the granule onto the skin or of a sufficient pressure being applied.

10. The granule according to claim 2, wherein the average diameter of the granule is between about 8 mm and about 15 mm.

11. The granule according to claim 1, wherein the core has a homogeneous composition from its central part to its periphery.

12. The granule according to claim 1, wherein the gum is a water soluble gum.

13. The granule according to claim 1, wherein the gum is selected from gum Arabic, carrageenans, alginates, pectins, karaya gum, xanthan gum, chitosan or derivatives thereof, hyaluronic acid, pullulan polymers or agar, dextran, celluloses and derivatives thereof, acrylic acid polymers cross-linked with an allyl ether, and mixtures thereof.

14. The granule according to claim 1, wherein the inert crystallized substance in the core is talc.

15. The granule according to claim 1, wherein the core contains residues in dry form of a liquid perfume that has been dried.

16. The granule according to claim 1, wherein the wax in the shell is selected from bees wax, carnauba wax, paraffin, microcrystalline wax, silicon wax, and mixtures thereof.

17. The granule according to claim 1, wherein the wax includes a mixture of bees and carnauba waxes.

18. The granule according to claim 1, wherein the crystallized substance in the shell is talc.

19. The granule according to claim 1, wherein the shell does not substantially include alcohol.

20. The granule according to claim 1, wherein the shell completely covers the core.

21. The granule according to claim 1, wherein the gum in the core is selected from gum Arabic, carrageenans, alginates, pectins, karaya gum, xanthan gum, chitosan or derivatives thereof, hyaluronic acid, pullulan polymers or agar, dextran, celluloses and derivatives thereof, acrylic acid polymers cross-linked with an allyl ether.

22. The granule according to claim 1, wherein the wax in the shell is selected from beeswax, carnauba wax, paraffin, microcrystalline wax, silicon wax, and mixtures thereof, and the crystallized substance in the shell is talc.

23. The granule according to claim 22, wherein the wax in the shell includes a mixture of bees and carnauba waxes.

* * * * *